(12) United States Patent
Friedman et al.

(10) Patent No.: US 9,669,136 B2
(45) Date of Patent: Jun. 6, 2017

(54) TISSUE REGENERATION MEMBRANE

(75) Inventors: Michael Friedman, Jerusalem (IL); Yoel Sasson, Rehovot (IL); Ada Grin, Rehovot (IL); Rami Mosheiff, Jerusalem (IL); Jacob Rachmilewitz, Modi'in (IL)

(73) Assignees: YISSUM RESEARCH DEVELOPMENT COMPANY OF THE HEBREW UNIVERSITY OF JERUSALEM, Jerusalem (IL); HADASIT MEDICAL RESEARCH SERVICES & DEVELOPMENT LTD., Jerusalem (IL)

(*) Notice: Subject to any disclaimer, the term of this patent is extended or adjusted under 35 U.S.C. 154(b) by 0 days.

(21) Appl. No.: 13/144,074

(22) PCT Filed: Jan. 12, 2010

(86) PCT No.: PCT/IL2010/000028
§ 371 (c)(1),
(2), (4) Date: Feb. 24, 2012

(87) PCT Pub. No.: WO2010/079496
PCT Pub. Date: Jul. 15, 2010

(65) Prior Publication Data
US 2012/0141430 A1 Jun. 7, 2012

Related U.S. Application Data

(60) Provisional application No. 61/193,947, filed on Jan. 12, 2009.

(51) Int. Cl.
| | |
|---|---|
| A61L 27/38 | (2006.01) |
| A61L 31/04 | (2006.01) |
| A61L 31/00 | (2006.01) |
| A61L 31/14 | (2006.01) |
| A61L 27/26 | (2006.01) |
| A61L 27/50 | (2006.01) |

(52) U.S. Cl.
CPC ............ *A61L 31/041* (2013.01); *A61L 27/26* (2013.01); *A61L 27/3834* (2013.01); *A61L 27/502* (2013.01); *A61L 31/005* (2013.01); *A61L 31/141* (2013.01)

(58) Field of Classification Search
USPC ............................................ 424/93.7; 1/93.7
See application file for complete search history.

(56) References Cited

U.S. PATENT DOCUMENTS

| | | | |
|---|---|---|---|
| 6,808,585 B2 * | 10/2004 | Boyce | A61F 2/28 |
| 7,108,862 B2 * | 9/2006 | Remington et al. | 424/426 |
| 2006/0115894 A1 * | 6/2006 | Wan | 435/325 |

FOREIGN PATENT DOCUMENTS

| | | |
|---|---|---|
| EP | 0489206 A1 | 6/1992 |
| EP | 0705878 A2 | 4/1996 |
| WO | 2006/127023 A2 | 11/2006 |
| WO | WO 2006127023 A2 * | 11/2006 |

OTHER PUBLICATIONS

Fujimori et al., Application of Eudragit RS to thermo-sensitive drug delivery systems II. Effect of temperature on drug permeability through membrane consisting of Eudragit RS/PEG 400 blend polymers. Journal of Controlled Release, vol. 102 (2005) pp. 49-57.*
Lin et al., PEG hydrogels for the controlled release of biomolecules in regenerative medicine. Pharmaceutical Research, vol. 26 No. 3 (online Dec. 18, 2008) pp. 631-643.*
Gupta et al., Development of matrix-membrane transdermal drug delivery system for atenolol. Drug Delivery, vol. 11 (2004) pp. 281-286.*
Carli et al., Surface and transport properties of acrylic polymers influencing drug release from porous matrices. International Journal of Pharmaceutics, vol. 21 (1984) pp. 317-329.*
Kulkarni et al., Effect of plasticizers on the permeability and mechanical properties of Eudragit films for transdermal application. Indian Journal of Pharmaceutical Sciences, vol. 64, No. 1 (2002) pp. 28-31.*
FDA Implants and Prosthetics. Datasheet [online]. Food and Drug Administration, 2013 [retrieved on Mar. 4, 2014]. Retrieved from the Internet: <URL: http://www.fda.gov/MedicalDevices/ProductsandMedicalProcedures/ImplantsandProsthetics/>.*
Kurian et al., Synthesis, permeability and biocompatibility of tricomponent membranes containing polyethylene glycol, polydimethylsiloxane and polypentamethycyclopentasiloxane domains. Biomaterials, vol. 24 (2003) pp. 3493-3503.*
Chakrabarty et al., Effect of molecular weight of PEG on membrane morphology and transport properties. Journal of Membrane Science, vol. 309 (online Oct. 26, 2007) pp. 209-221.*
Aggarwal et al., Human mesenchymal stem cells modulate allogeneic immune cell responses. Blood, vol. 105, No. 4 (Feb. 15, 2005) pp. 1815-1822.*
'Flexible'. Merriam-Webster Dictionary [online]. Merriam-Webster Inc., 2015 [retrieved on Jul. 19, 2016]. Retrieved from the Internet <URL: http://www.merriam-webster.com/dictionary/flexible>.*
Ghaffari et al., "Preparation and characterization of free mixed-film of pectin/chitosan/Eudragit RS intended for sigmoidal drug delivery", European J. of Pharmaceutics and Biopharmaceutics 67(1):175-86 (2007).

* cited by examiner

*Primary Examiner* — Kara Johnson
(74) *Attorney, Agent, or Firm* — Browdy and Neimark, PLLC

(57) ABSTRACT

The present invention relates to a membrane comprising at least one positively charged, synthetic, hydrophobic polymer, at least one hydrophilic polymer and at least one plasticizer; wherein said membrane is flexible and is capable of supporting at least one of cell adherence, cell proliferation or cell differentiation. The invention further relates to use of a membrane of the invention in the preparation of an implantable devices including cell delivery systems, cell growing surfaces and scaffolds. The invention further provides methods for promoting tissue regeneration in a defected tissue region applying membranes of the invention.

26 Claims, 14 Drawing Sheets

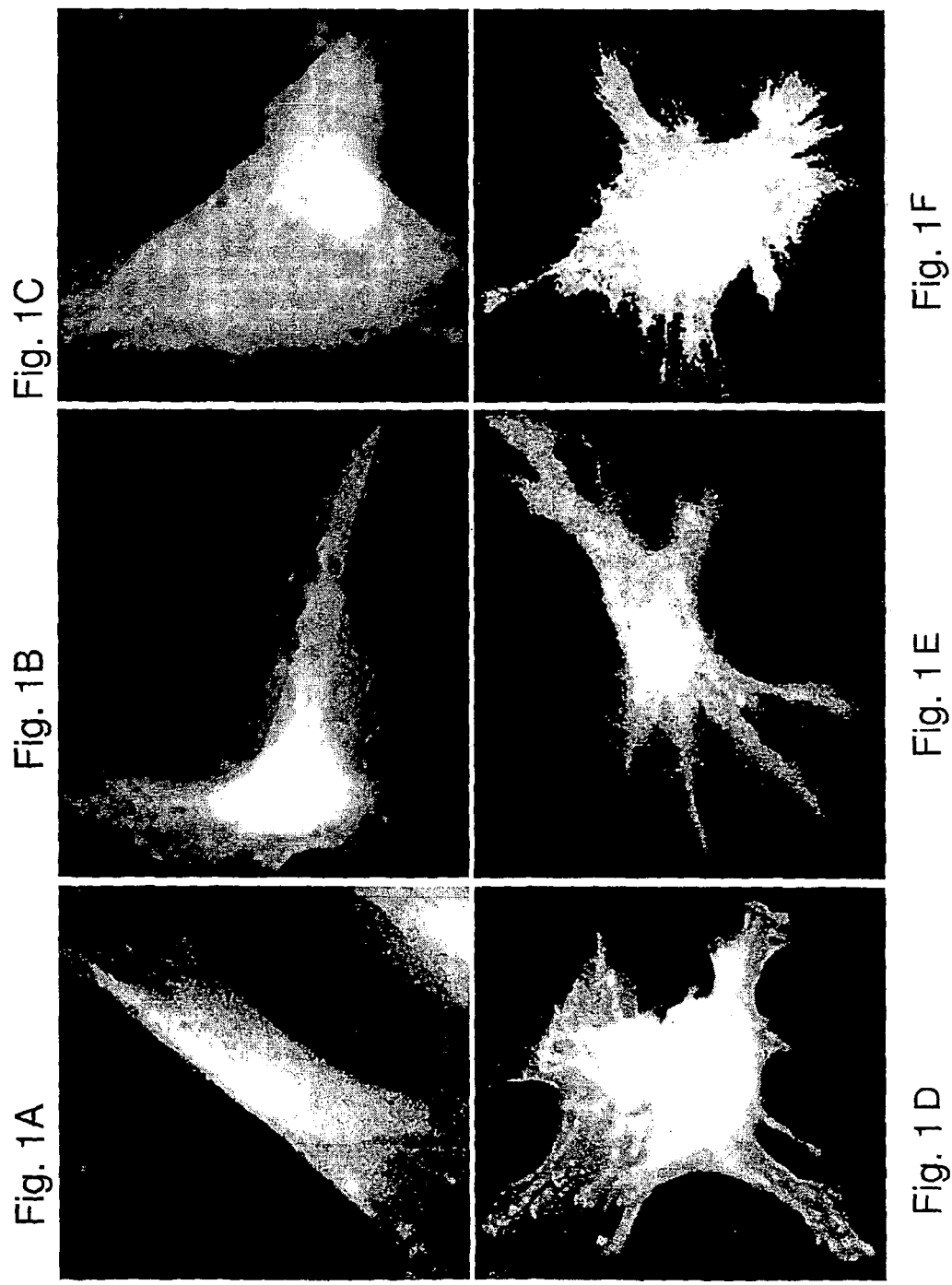

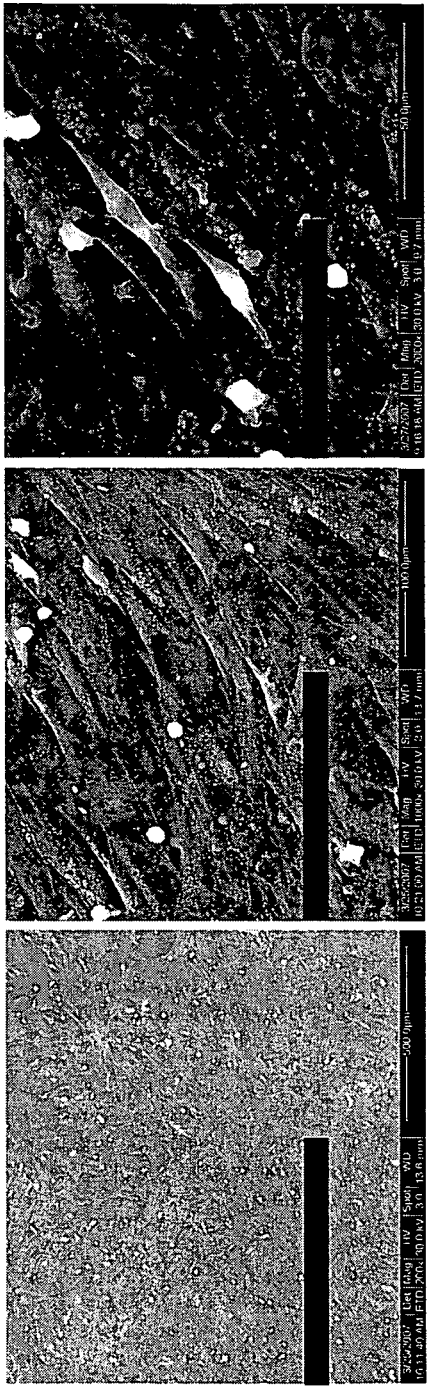

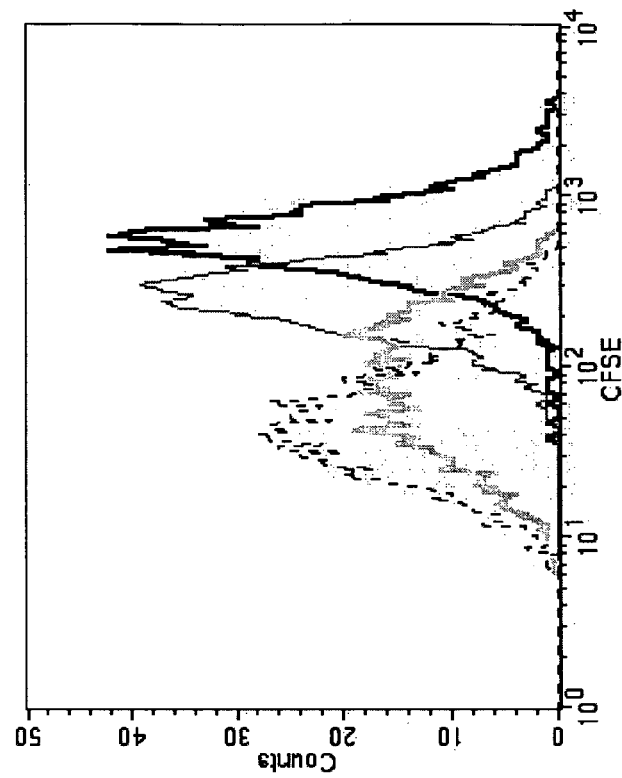
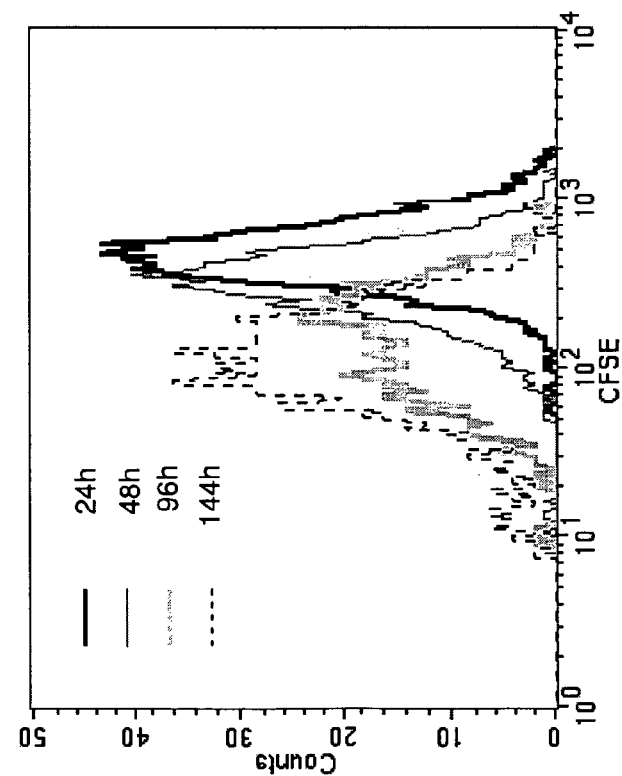
Fig. 3A
Fig. 3B

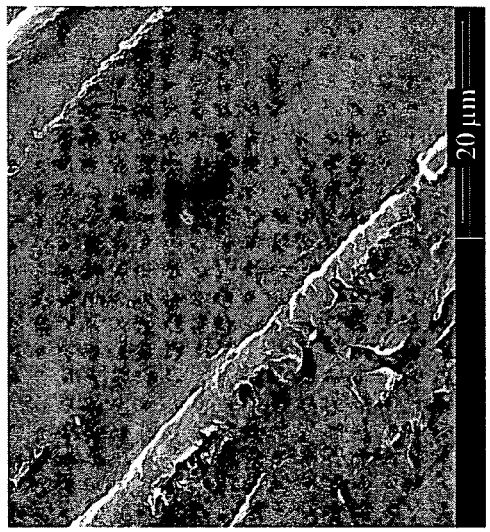
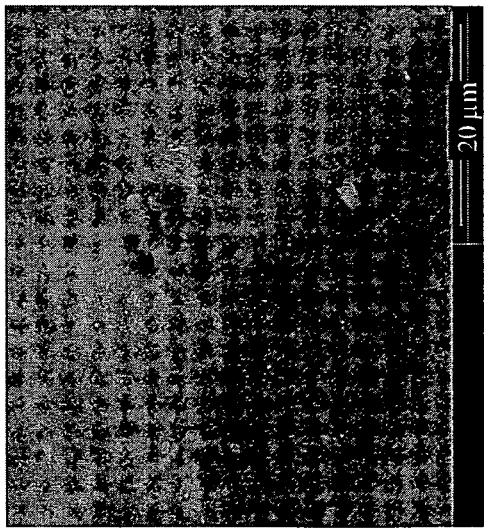
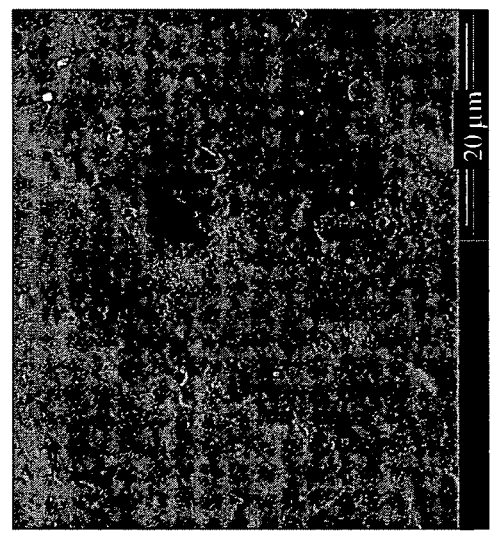
Fig. 5A
Fig. 5B
Fig. 5C

TISSUE REGENERATION MEMBRANE

CROSS-REFERENCE TO RELATED APPLICATIONS

This application is a U.S. National Stage Application of International Application No. PCT/IL2010/000028, filed Jan. 12, 2010, which claims the benefit under 35 U.S.C. 119(e) of U.S. Provisional Application No. 61/193,947, filed Jan. 12, 2009.

FIELD OF THE INVENTION

This invention relates to the field of tissue regeneration, specifically bone regeneration, using a polymer based membrane or construct capable of supporting cell adhesion, proliferation and differentiation.

BACKGROUND OF THE INVENTION

Non union of the fracture is the condition of cessation of all reparative processes of healing of fracture without bone union [1-3]. Non union can also be described as the absence of progressive repair that has not been observed radiographically between the 3rd and the 6th month following the fracture [2, 4]. Non-union may occur either as a result of poor mechanical or biological environment on the fracture area or as a combination of the two [2]. This and other situations require manipulation or augmentation of natural healing mechanisms to regenerate large quantities of new bone than would naturally occur to achieve surgical goals [5-7]. Therefore, new bone for the repair or the restoration of the function of traumatized, damaged, or lost bone is a major clinical need, and bone tissue engineering has been heralded as an alternative strategy for regenerating bone [8].

Tissue engineering, as it applies to bone, focuses on restoration of large segments of skeleton including weight bearing bones. Bone can be regenerated through the following strategies: Osteogenesis—the transfer of cells; Osteoinduction—the induction of cells to become bone; Osteoconduction—providing a scaffold for bone forming cells; or Osteopromotion—the promotion of bone healing and regeneration by encouraging the biologic or mechanical environment of the healing or regenerating tissues.

A polymeric poly (L-lactide) tubular membrane spanning a mechanically stable, large segmental bone defect was shown to promote woven bone formation and reconstruction of the bone defect [9]. Mosheiff et al. developed a critical size defect model in rabbit for bone loss treatment testing. In this model the rabbit forearm is to produce critical size defect. A critical size defect is defined as the smallest intraosseus wound that is not bridged by the skeleton in normal circumstances [10, 11]. Using this model, our group has successfully employed membranes for guided bone regeneration (GBR), by osteoconduction [10, 12].

Gugala et al. demonstrated homogenous growth of mesenchymal stem cells (MSC) on porous membranes, forming a three-dimensional fibrillar network [19].

WO 2005/107826 discloses moldable bone implants comprising biocompatible granules (e.g. bioceramics), a biocompatible polymer and a plasticizer. The implant may form an open porous scaffolding or composite matrix or may be administered as a liquid or plastically deformable implant.

WO 2004/084968 discloses a porous matrix suitable for use as a tissue scaffold or an injectable formulation, preferably prepared from a degradable cross-linked polymer.

SUMMARY OF THE INVENTION

The present invention is based on the finding that a novel polymer-based membrane, comprising both hydrophobic and a hydrophilic polymers and which further comprises a plasticizer, is capable of supporting cell adhesion, proliferation and differentiation, and thus can be used to augment tissue regeneration, for example in the treatment of large segmental bone defects. The membranes of the invention operate both as a delivery system for cells and as a device for guided bone regeneration, optionally together with active agents that promote cell growth, adhesion, differentiation, and/or proliferation.

Specifically, the invention is based on the finding that a polymer-based membrane which further comprises polyethyleneglycol (PEG) supported mesenchymal stem cell (MSC) adhesion, differentiation, and proliferation.

Accordingly, in one of its aspects the invention provides a membrane comprising at least one positively charged, synthetic, hydrophobic polymer, at least one hydrophilic polymer and at least one plasticizer; wherein said membrane is flexible and is capable of supporting at least one of cell adherence, cell proliferation or cell differentiation.

As used herein the term "membrane" concerns a thin (roughly two dimensional) continuous homogenous construct having a thickness of between 30-200 µm, typically constructed by casting at least one positively charged synthetic, hydrophobic polymer, at least one hydrophilic polymer and at least one plasticizer into molds.

The term "positively charged synthetic, hydrophobic polymer" relates to a synthetically produced polymer which is insoluble in water, having an overall average positive (surface) charge resulting from positively charged or partially positively charged monomer groups (or substituents on said monomers) of the polymer.

In some embodiments, said at least one hydrophobic polymer is an acrylic polymer. In other embodiments, said at least one hydrophobic polymer is a methacrylate copolymer substituted by at least one amine group. The term "amine group" is meant to encompass any amine group such as for example —$NH_3$, a secondary amine, tertiary amine and an ammonium group. In a specific embodiment said polymer is Ammonic Methacrylate Copolymer, and more preferably Ammonic Methacrylate Copolymer type A (for example, AMCA EUDRAGIT® RL Degussa Germany).

It should be understood that a hydrophobic polymer in accordance with the invention also encompasses co-polymers, or mixture of hydrophobic, positively charged polymers with hydrophobic non-positively charged polymers, for example, wherein at least 30% of the hydrophobic polymer has a positive charge. In such embodiments, the mixture of hydrophobic polymers may further include polyethylene, polymethacrylate, polyamide-nylon, polyethylene vinyl acetate, cellulose nitrate, silicones, ethylcellulose and any combination thereof.

As used herein the term "polymer having an amine group and a methacrylic group", concerns polymers as well as copolymers having as monomers methacrylic groups substituted with amine groups. Example of such polymers can be found, for example, in Aggeliki I. et al [20].

The term "hydrophilic polymer" refers to polymers (including co-polymers and mixtures of polymers) that dissolve in aqueous media such as in bodily fluids (e.g. extracellular fluid, interstitial fluid, plasma, blood, or saliva). It is noted that such polymers generate pores in the membrane upon exposure to aqueous media.

In some embodiments, said at least one hydrophilic polymer is selected from the group consisting of hydroxylpropylmethylcellulose, hydroxylpropylcellulose, carboxymethylcellulose, hydroxyethylcellulose, polyvinyl alcohol, polysaccharides, sodium alginate, polyvinylpyrrolidone, modified starch, polyethylene glycol, polyethylene oxide and gelatin.

The term "plasticizer" relates to a compound capable of endowing the membrane with flexibility. A plasticizer used in accordance with the present invention should be non-toxic to cells. In some specific embodiments said plasticizer is non-toxic to stem cells.

In some embodiments, said at least one plasticizer is selected from the group consisting of polyethylene glycol, polyethylene oxide, triethyl citrate, acetyl triethyl citrate, tributyl citrate, acetyl tributyl citrate, triacetin, dibutyl sebacate, diethyl phthalate, propylene glycol, methoxyethylene glycol and gelatin.

In some embodiments, the membrane of the invention comprises at least one plasticizer that is water soluble. Non-limiting list of water soluble plasticizers includes: PEG, triethyl citrate, acetyl triethyl citrate, tributyl citrate, acetyl tributyl citrate, triacetin, dibutyl sebacate, diethyl phthalate, propylene glycol, methoxyethylene glycol and gelatin.

In some embodiments said at least one plasticizer and at least one hydrophilic polymer are compatible with stem cells.

As will be demonstrated in the examples below PEG was shown to be non toxic to stem cells. Therefore, in a specific embodiment wherein the membrane includes stem cells the preferred plasticizer and/or hydrophilic polymer is PEG.

The term "polyethylene glycol (PEG)" refers to polyethylene glycol polymers that dissolve in aqueous media. In some embodiments PEG in the range of 300-20,000 is used in a membrane of the invention. In other embodiments PEG 400 is used in a membrane of the invention.

In some embodiments said hydrophilic polymer is polyethylene glycol ranging from 300-20,000. In other embodiments said plasticizer is polyethylene glycol ranging from 300-20,000. In yet further embodiments both said hydrophilic polymer and said plasticizer are polyethylene glycol ranging from 300-20,000.

Without wishing to be bound by theory, in such cases PEG appears to carry out a dual function in the membrane; it contributes flexibility to the membrane and it causes pore creation upon dissolution. As demonstrated in the Examples below, porosity (number of pores in the membrane) increases according to PEG concentrations within the membrane. Furthermore, an increased porosity correlates with increased cell adhesion.

In other embodiments of the invention, said at least one hydrophilic polymer is present in a concentration of between about 0.5% weight/weight (w/w) to 30% (w/w) of the membrane. In other embodiments, said at least one hydrophilic polymer is present in a concentration of between about 10% (w/w) to about 25% (w/w) of the membrane.

In a specific embodiment, said at least one hydrophilic polymer is selected from the group consisting of hydroxylpropylmethylcellulose, hydroxylpropylcellulose, carboxymethylcellulose, hydroxyethylcellulose, being in a concentration of between about 0.5% (w/w) to 20% (w/w) of the membrane.

In another specific embodiment, said at least one hydrophilic polymer is PEG, being in a concentration of between about 1% (w/w) to 30% (w/w), or between about 10% (w/w) to about 25% (w/w), or about 15% (w/w) of the membrane.

In a further embodiment a membrane of the invention further comprises at least one type of cell. In some embodiments, said cells are selected from the group consisting of adult stem cells, embryonic stem cells, pluripotent stem cells, mesenchymal stem cells, umbilical cord blood cells, osteoblasts, chondroblasts and CD105+ cells. In other embodiments, said stem cells are autologous adult stem cells.

Pluripotent mesenchymal stem cells have the capacity to undergo commitment to several cell lineages, including osteoblasts, adipocytes, chondrocytes, and myocytes.

In one embodiment a membrane of the invention comprises AMCA, polyethylene glycol ranging from 300-20,000 (in an amount sufficient to be both a plasticizer and a hydrophilic polymer capable of forming pores upon contact with aqueous fluids in situ), and adult stem cells.

As used herein the term "cell adhesion" or "cell adherence" refers to the binding/attachment of a cell to a surface while maintaining viability.

As used herein the term "cell proliferation" or "cell growth" refers to reproduction and increase in cell number, i.e. cell division.

As used herein the term "cell differentiation" refers to a process by which a less specialized cell becomes a more specialized cell type. For example, adult stem cells divide and create fully-differentiated daughter cells during tissue repair and during normal cell turnover, e.g. mesenchymal stem cells may differentiate into osteoblasts.

The membranes of the invention are capable of supporting cell adherence, cell proliferation and/or cell differentiation.

Membranes according to the present invention exhibit qualities such as the ability to (i) develop direct adhesion and bonding with existing tissue; (ii) promote cellular function; (iii) provide a scaffold or template for the formation of new tissue; and (iv) promote tissue regeneration and act as a carrier for bioactive materials.

In some embodiments, a membrane of the invention further comprises at least one active agent capable of promoting tissue reproduction and/or deliver pharmaceutical benefits needed in the site of implantation of said membrane.

In other embodiments, a membrane of the invention further comprises at least one active agent, wherein said at least one active agent is selected from the group consisting of cytokine, hormone, bisphosphonate, cannabinoid, beta blocker, bone inducing agent, growth factor, HMG-CoA reductase inhibitor (such as statins), drug and antibiotic, and any combinations thereof.

In some embodiments said active agent is selected from the group consisting of statin, estrogen, androgen, propranolol, transforming growth factor (TGF), bone morphogenetic protein (BMP, such as for example BMP-2 and BMP-7), insulin like growth hormone, fibroblast growth factor (FGF), alendronate, risendronate and parathyroid hormone. In yet further embodiments, said active agent is simvastatin or lovastatin.

Simvastatin is a member of the statin family of 3-hydroxy-3-methyl-glutaryl coenzyme A reductase inhibitors, which are widely used as cholesterol-lowering drugs. Statins may increase bone mass by anabolic and anticatabolic (antiresorptive) mechanisms.

In some embodiments said agent is in a controlled release formulation.

In another specific embodiment, the membrane comprises AMCA, PEG and at least one active agent (e.g. simvastatin).

In some embodiments a membrane of the invention is capable of being porous upon hydration (for example hydration achieved upon contact with bodily fluids in the implantation site), and wherein the pore size is between about 0.1 to about 5 microns.

In some embodiments a membrane of the invention may have at least one pore due to hydration of said water soluble plasticizer in a size of less than 5 microns. In other embodiments said pore size is less than 2 microns. In yet other embodiments said pore size is between about 0.1 to about 5 microns.

As used herein the term "hydration" refers to exposure of the membrane of the invention to aqueous solution or a body fluid, e.g. interstitial fluid, blood, plasma, saliva, which results in dissolution of the water soluble plasticizer.

In another aspect, the invention provides a use of a membrane of the invention, for the preparation of a three dimensional hollow implant for tissue regeneration of a defected tissue region.

Due to the flexibility of a membrane of the invention it is possible to form a three dimensional implant using said membrane, without the need to pre-casting or re-molding the membrane or exposing it to heat. The three dimensional structure constructed from said membrane may be any type of structure suitable for the site of implantation, and may further be adjusted at the site of implantation in accordance with the area wherein said implant is to be used.

In some embodiments, said three dimensional hollow implant is selected from the group consisting of a tubular implant, a cylindrical implant, a conical implant or a planar implant.

In a further embodiment, said tissue to be regenerated upon use of a membrane of the invention or a three dimensional hollow implant made thereof, is selected from ligament, tendon, cartilage, intervertebral disc, dental tissue (including teeth, enamel, dentin, cementum, pulp, periodontal ligaments, alveolar bone, gingiva tissue) and bone.

In a further aspect the invention provides a three dimensional hollow implant comprising at least one membrane of the invention. In one embodiment, a membrane of the invention comprised within a three dimensional hollow implant of the invention defines the surface of the implant.

In another aspect the invention provides a cell delivery system comprising a membrane of the invention.

In yet a further aspect the invention provides a cell growing surface comprising a membrane of the invention.

In another one of its aspects the invention provides a scaffold substantially coated by a membrane of the invention.

The invention also provides granular material substantially coated by a membrane of the invention. In certain embodiments, the granular material is composed of bone compatible ceramics e.g. calcium-based minerals.

The invention further provides a method for promoting tissue regeneration in a defected tissue region comprising the steps of: providing a membrane of the invention; and implanting said membrane in the proximity of said tissue defect region. In some embodiments said defected tissue results from a condition selected from non-union fracture, osteoporosis, periodontal disease or condition, osteolytic bone disease, post-plastic surgery, post-orthopedic implantation, post neurosurgical surgery, alveolar bone augmentation procedures, spine fusion, vertebral fractures.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A-1F shows micrographs of hMSC adherence on polystyrene tissue culture dish and on AMCA membrane. CFSE-labeled hMSC were seeded either on polystyrene tissue culture dish (A-C) or on membrane (D-F). After 24 h CFSE-labeled cells were visualized by confocal microscopy. Three representative images for each culturing condition are shown.

FIGS. 2A-2F shows scanning electron micrographs of the hMSC adherence on AMCA/PEG membranes. hMSC were seeded on AMCA membrane with PEG 400. After 24 h in culture cells were fixed as described in Materials and Methods and analysis was performed using scanning electron microscopy (SEM). Magnifications of images from left to right are: upper panel—×200 (FIG. 2A), ×1000 (FIG. 2B), ×2000 (FIG. 2C); ×4000 (FIG. 2D), ×5000 (FIG. 2E), ×6000 (FIG. 2F).

FIGS. 3A-3B shows flow cytometric analysis of CFSE labeled hMSC. $1 \times 10^5$ CFSE-loaded hMSC were cultured on either AMCA membrane with 15% PEG 400 (FIG. 3A) or polystyrene tissue culture dish (FIG. 3B) for 24 h, 48 h, 96 h and 144 h. At the indicated time points cells were harvested and flow cytometric analysis was performed. Loss of CFSE reflects cellular division.

FIGS. 5A-5C show scanning electron micrographs of the AMCA membranes: Membranes were prepared using solvent casting technique. The membranes were then analyzed using SEM or immersed in phosphate-buffered saline (PBS) for 24 h and then analyzed by SEM. (FIG. 5A): 15% PEG 400 membrane before immersion in PBS—showing no porosity; (FIG. 5B): membrane with 5% PEG after immersion in PBS—slightly porous; (FIG. 5C): Membrane with 15% PEG after immersion in PBS—porous. Magnification: ×5000.

(FIG. 6A): Control polystyrene dish; (FIG. 6B): AMCA membrane with 15% PEG 400.

membrane which contained simvastatin; Contralateral limb was inserted with EC membrane. Calibration was done using Osirix software.

Figure 9:
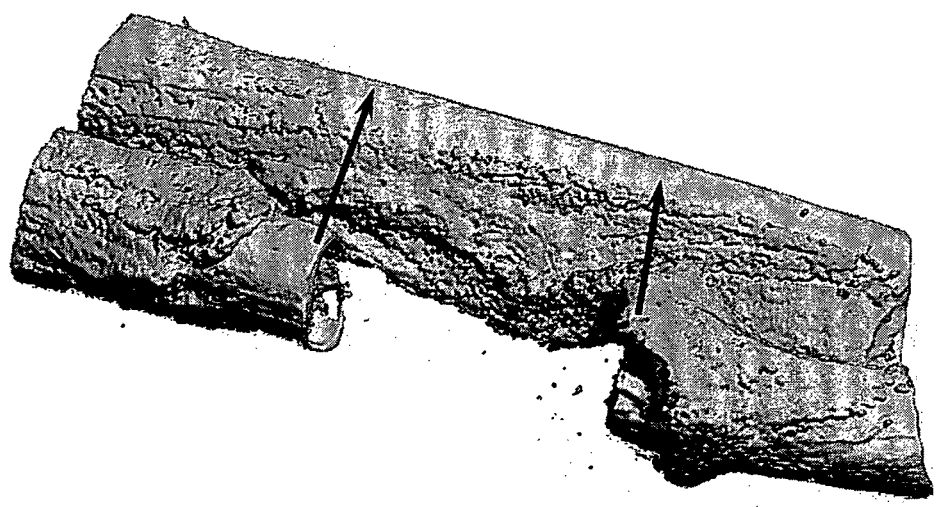

FIG. 9 shows a microCT of bone regeneration with EC membrane. In this experiment bone defect was left untreated. The bone defect was in a non union state. Arrows mark the bone defect area.

Figure 10:

FIG. 10 shows microCT (computed tomography) of bone regeneration with EC membrane containing simvastatin. In this experiment bone defect was treated and successful bridging of the defect was shown. Arrows mark the bone defect area.

Figure 11A:
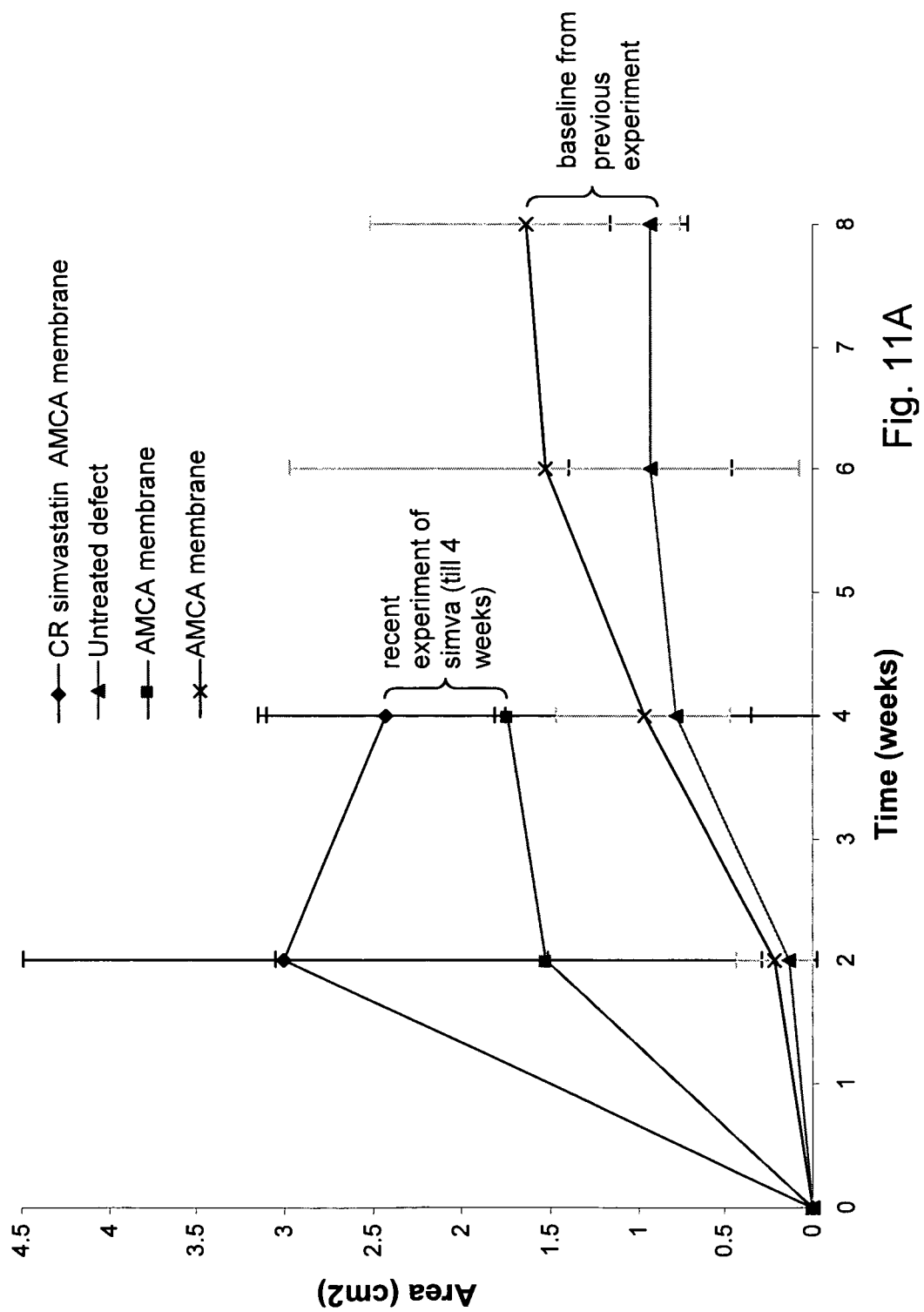
Figure 11B:
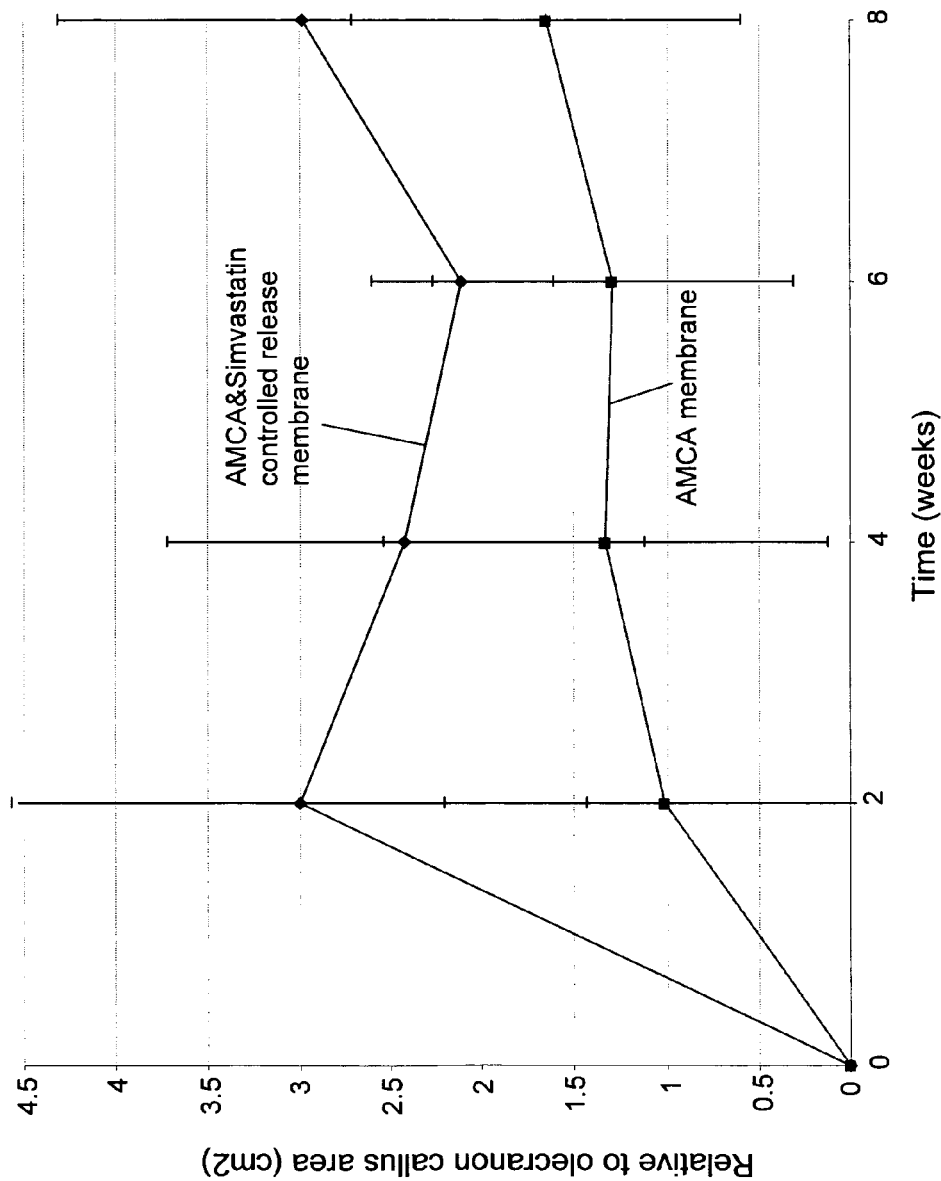

FIGS. 11A-11B is a graph showing mean callus area growth for AMCA membrane of the invention, with and without addition of controlled release simvastatine. A—Shows results obtained 4 weeks after implantation of the AMCA membrane+simvastatin. B—Shows results obtained 8 weeks after implantation of the AMCA membrane+simvastatin FIGS. 12A-12D is a graph showing various parameter effects on simvastatine release from membrane of the invention (measured in vitro): effect of simvastatin concentration on simvastatin release rate (FIG. 12A); effect of membrane width on simvastatin release rate (FIG. 12B); effect of plasticizer on simvastatin release rate (FIG. 12C); effect of plasticizer type on simvastatine release rate (FIG. 12D).

Figure 13A:
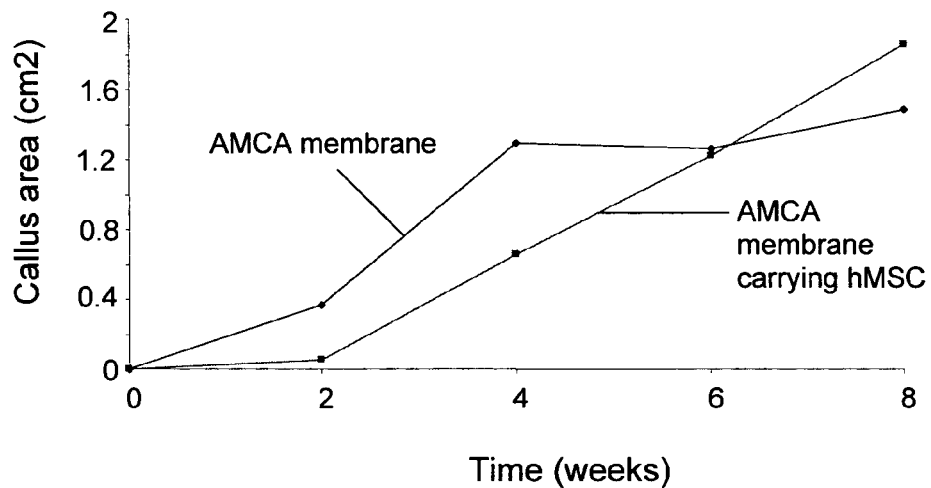
Figure 13B:
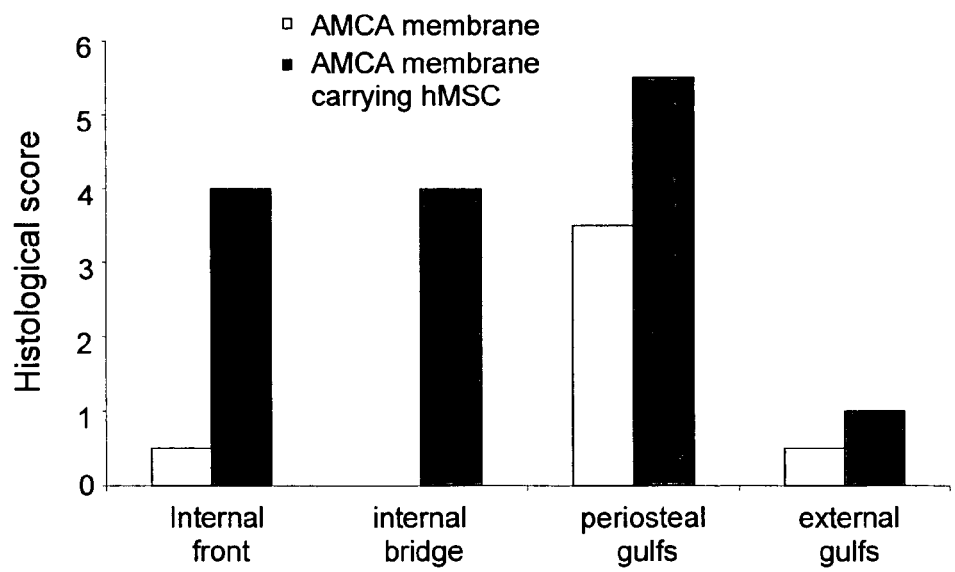

FIGS. 13A-13B is a graph showing bone regeneration parameters achieved with AMCA membrane carrying hMSC in rabbit critical size defect model. FIG. 13A shows callus area growth. FIG. 13B shows a histological evaluation of defects after 8 weeks from implantation of membrane.

DETAILED DESCRIPTION OF EMBODIMENTS

The present invention provides a membrane composed of at least three elements, the first being a synthetic, hydrophobic polymer having a positive surface charge, which is non-biodegradable under physiologic conditions, at least one hydrophilic polymer which is biodegradable under physiological conditions and at least one plasticizer. Without wishing to be bound by theory, the combination of these elements generates a membrane which is flexible enough to be able to generate three dimensional structures suitable for various therapeutic applications, for example, a hollow tube. Moreover, upon exposure to fluid (in vivo or ex vivo), the hydrophilic polymer at least partially disintegrates and the membrane becomes porous, thus enabling the adhesion of cells.

Cells may be seeded on a membrane of the invention as will be further described below in detail.

In further embodiments, a membrane of the invention may further include an active agent, as further detailed below.

A membrane of the invention can serve as an infrastructure to allow guided tissue repair as well as a cell delivery system. A membrane of the invention may also serve as a barrier membrane for eliminating infiltration of unwanted cells, blood vessels and soft/scar tissue into the treated area, and for isolating the cells delivered in said membrane from the surrounding tissue, and preventing the leakage of cells and factors from the space inside the membrane to the surrounding tissue.

A membrane of the invention may be used as such, for example, by covering a region into which the cells are delivered, however, in certain embodiments it may be used to form a three dimensional device (for example a hollow tubular device) which holds the cells to be deliver, or may coat a tissue engineering scaffold containing the cells to be delivered.

In some embodiments, a membrane of the invention is folded into a desired three dimensional structure, e.g. a tubular device. The tubular device can be used as an infrastructure to allow guided tissue repair as well as to deliver cells into a tubular region of defect, such as a bone defect, and the membrane can be used to hold the delivered cells and components in the device and prevent infiltration of cells, extracellular matrix and blood vessels from the surrounding tissue into the space surrounded by the device.

In other embodiments, a membrane of the invention is used for coating a tissue engineering scaffold. Such a membrane-coated scaffold can hold cells to be delivered into a site in the body. The membrane coating isolates the cells delivered in the scaffold from the surrounding tissue and prevents the leakage of cells, and soluble factors from the space inside the scaffold into the surrounding tissue. Coating of the scaffold with a membrane of the invention may allow better cell adhesion and higher doses of cells to be delivered to the target site.

In yet other embodiments, a bone defected area can be wrapped after implantation of a scaffold with a membrane of the invention in order to prevent leakage of cells and soluble factors and to prevent growth of soft tissue into the scaffold.

The term "cell delivery" refers to introduction of cells into a desired site in the body of an individual for therapeutic purposes.

A membrane of the invention is suitable for seeding of any type of cells for example stem cells (both adult and embryonic stem cells). In other embodiments cell type may be selected from the following non-limiting list: mesenchymal (stromal) stem cells, umbilical cord blood cells, osteoblasts, chondroblasts, or CD105+ cells. The invention also encompasses seeding of pluripotent stem cells of embryonic origin as well as adult cells that have been reprogrammed to become pluripotent. The cells may be autologous, allogenic or xenogenic.

In some embodiments, the cells are autologous adult stem cells, obtained, for example, from bone marrow or adipose tissue.

Cell seeding is performed in some embodiments ex vivo. The cells may be placed on the membranes (for example formed as a hollow tubular device) or placed in a tissue engineering matrix (also termed herein "scaffold") coated by the membrane of the invention. Examples of tissue engineering matrix are those fabricated from either biological materials or synthetic polymers.

In certain embodiments, a membrane of the invention, a tubular implant of the invention or a coated scaffold of the invention, with or without ex vivo seeded cells are placed at a desired location in the body. This location is typically a location where it is desired to generate new tissue which has been damaged by trauma, surgical interventions, genetic or disease processes.

In some embodiments a desired site is a site where tissue should be generated from adult stem cells; is some embodiments such a site is ligament, tendon, cartilage, intervertebral disc, dental tissue or bone tissue, most preferably bone tissue.

Generation of bone tissue is required in conditions such as non-union fractures, osteoporosis, periodontal disease or teeth implantation, osteolytic bone disease, post-plastic surgery, post-orthopedic implantation, post neurosurgical surgery that involves calvaria bone removal, in alveolar bone augmentation procedures, for spine fusion and in vertebral fractures.

Generation of tendon/ligament tissue is required for example following tissue tear due to trauma or inflammatory conditions.

Generation of cartilage tissue is required in conditions such as Rheumatoid Arthritis, Osteoarthritis, trauma, cancer surgery or cosmetic surgery.

Generation of intervertebral disc tissues including nucleous pulposus and annulus fibrosus, is required in conditions such as nucleous pulposus degeneration, annulus fibrosus tears, or following nucleotomy or discectomy.

Typically the membrane, for example in the form of a hollow tube is placed at the desired site by implantation.

In certain embodiments, the membrane of the invention comprises a synthetic, hydrophobic positively charged polymer, a hydrophilic polymer, a plasticizer and an active agent and is further seeded with cells.

In a specific embodiment the membrane of the invention comprises a synthetic, hydrophobic positively charged polymer and PEG and is further seeded with stem cells.

As used herein the term "cell-growing surface" refers to any artificial surface suitable for cell growth for example a slide, vessel or cell/tissue culture dish. The membrane coated cell growing surface in accordance with the invention thereby gains properties suitable for cell adhesion, proliferation and/or differentiation.

The present invention provides a flexible membrane capable of supporting MSC adherence, proliferation and differentiation. Such a membrane can be used as treatment for bone regeneration applications. The healing of displaced fractures and regeneration of bone defects does not result only from proliferation of the locally present osteoblasts, but involves recruitment, proliferation, and differentiation of preosteoblastic cells. The differentiation of multipotent osteoblastic precursors is the main initial event in bone healing and callus formation, although preexisting osteoblasts might also be involved. Any failure in the recruitment, establishment, proliferation, and differentiation of these progenitor cells can lead to delayed union or nonunion. There are many difficulties related to the healing of critical-size bone defects. In general, these difficulties result from the fact that there is an insufficient number and/or activity of osteogenic cells of the host to allow for healing.

A membrane of the invention can guide bone regeneration as well as prevent unwanted vascularization in the newly formed bone. The membrane can also protect the area of bone defect from infiltration by connective and scar tissues, guide the osteogenic cells and allow storage of osteogenic components in the space enclosed by the membrane, which may potentially be released from the bone ends and bone marrow [10, 12]. Furthermore, placing MSC attached to a membrane at the site of critical size defect model will provide starting material for a new bone tissue. Therefore, implanting GBR membrane with expanded ex vivo MSC may greatly improve the bone repair outcome.

As demonstrated in the Examples provided below, several polymers were tested in conjugation with various plasticizers.

In one embodiment, a membrane constituted from AMCA and 15% PEG 400 could support good MSC adhesion, proliferation and differentiation: (I) MSC adhered to AMCA membrane with 15% PEG 400 as determined by light microscopy, fluorescent microscopy and SEM. (II) MSC maintain their proliferative activity as determined by CFSE labeling and flow cytometric analysis (III) MSC maintained their differentiation ability as determined by Alizarin Red staining.

AMCA membrane containing 15% PEG 400 supported MSC differentiation to osteoblasts.

Materials and Methods

Polymers:

Ammonio Methacrylate Copolymer type A NF (AMCA, EUDRAGIT® RL, Degussa, Germany) and Ethyl Cellulose (EC, ETHOCEL® N 100, Hercules Inc., Wilmington, Del.).

Plasticizers:

Polyethylenglycol 400 (PEG 400, Merck, Germany), Glyceryl triacetate (Triacetin, Fluka, Rehovot, Israel), Glycerin (Frutarom, Israel), Triethyl Citrate (Fluka, Rehovot, Israel), Dibutyl Sebacate (Fluka, Rehovot, Israel), Dibutyl Phtalate (Fluka, Rehovot, Israel).

Polymeric Membranes Preparation and Sterilization—

Membranes were prepared using solvent casting technique as disclosed in Friedman M. and Golomb G. J. [13]. Polymeric membranes were cast from solution consisting of polymer, plasticizer and Ethanol (Frutarom, Israel) into TEFLON® moulds (round plates, inner diameter 9.6 cm) and the solvent was allowed to evaporate over night. Membranes width was: 100±5 µM.

Prior to use in tissue culture, membranes were immersed in PBS (Biological Industries, Beit Haemek, Israel) for 24 hours to wash out possible remains of ethanol and then sterilized by UV irradiation for 2 hr.

Characterization of Membranes—Scanning Electron Microscopy (SEM) Photomicrographs—

AMCA membranes containing 15% PEG 400 were fixed with 2% glutaraldehyde in cocodylate buffer (0.1 M; pH=7.2) for 2 hours. The specimens were then processed according to the air drying method skipping the ethanol dehydration series (Ethanol dissolves AMCA; therefore it should be excluded from the specimen preparation). The process was accomplished through 100% Freon 113. The specimens were vigorously shaken, which allowed rapid evaporation of the Freon phase. The membranes were mounted in copper stubs, coated with gold and then examined in FEI quanta 200 at an accelerating voltage of 30 KV.

Cell Harvesting and Culture— hMSCs were obtained from discarded bone tissues from patients undergoing total hip replacement surgeries, under approval of Hadassah Medical Center Helsinki Ethics Committee following an informed consent.

The hMSCs were separated from other bone marrow-residing cells by plastic adherence and were then grown under tissue culture conditions, as described in Krampera M. et al. [14], and Djouad F et al [15]. The cells were maintained in a low-glucose Dulbecco's Modified Eagle Medium (DMEM) supplemented with 10% heat-inactivated fetal calf serum, 2 mM glutamine, and penicillin/streptomycin (Biological Industries, Beit-Haemek, Israel). Primary cultures were usually maintained for 12-16 days, and were then detached by trypsinization and subcultured (Barry F P. et al. [16]). The medium was changed every 3-4 days.

MSC Adhesion to Membrane—

For MSC labeling, MSC were re-suspended in PBS ($10^7$ cells/ml) containing 5-carboxyfluorescein diacetoxymethyl ester (BCECF/AM or CFSE; 5 µg/mL; Calbiochem), incubated at 37° C. for 10 mM, and the cells were then washed three times. Cells were cultured on a sterilized membrane wetted with PBS, $15 \times 10^4$ cells in 150 µl medium, and incubated for six hours at 37° C. Afterwards 3 ml of medium were added. Cells were examined 24 hours after seeding by fluorescent microscope. Tissue culture polystyrene dishes were used as a positive control for membrane in cell adhesion test.

CFSE-Based Proliferation Assay—

For cell division studies, MSC were resuspended in PBS ($10^7$ cells/ml) containing 3'-O-Acetyl-2',7'-bis(carboxyethyl)-4 or 5-carboxyfluorescein diacetoxymethyl ester (BCECF/AM or CFSE; 5 µg/mL; Calbiochem), incubated at 37° C. for 10 min, and washed three times. CFSE-labeled cells were then seeded on the membrane or on the tissue culture dishes as described above. At the indicated time points cells were harvested and proliferation of cells was visualized by incremental loss of CFSE fluorescence as analyzed on a FACSCalibure flow cytometer (Becton Dickinson) using Cell Quest software.

MSC Differentiation on Membrane—

MSC were seeded on the membranes or on the center well organ culture dishes (Falcon) for control, as described above. As soon as MSC were confluent, the culture medium was supplemented with ascorbic acid (50 µg/ml), dexamethasone ($10^{-8}$ M) and β-glycerophosphate (10 mM). Medium was changed twice a week for 17 days, afterwards membranes and dishes were dyed with Alizarin Red, as described below.

Alizarin Red Staining—

A stock solution of 2% alizarin red in distilled water was adjusted to pH 4.2 with NaOH and passed through a 0.22 µm filter. Cultures in the center well organ culture dishes were rinsed with 150 mM NaCl three times, fixed in ice cold 70% ethanol, rinsed with distilled water and stained at room temperature for 10 min with 500 µl of alizarin red stock per well. Individual wells were rinsed five times with distilled water; a sixth and final wash with distilled water was performed for 15 min (Halvorsen Y D. et al. [17]). Membranes due to their positive charge had a higher affinity towards alizarin red stain than a negatively charged center well organ culture dishes, therefore rinsing with distilled water didn't remove the stain from the membranes well enough. To reduce background we applied a single rinse with 0.02 M HCl on the membranes. Photomicrographs were then obtained.

Example 1—Cell Adhesion Using a Membrane of the Invention

Various membranes were tested for their ability to support cell attachment and growth. The tested membranes varied in their polymer and plasticizer types. Several plasticizers were tested, i.e. glycerin, polyethylene glycol, triethyl citrate, dibutyl sebacate, dibutyl phtalate, triacetin. The plasticizers tested were hydrophobic or hydrophilic and were added in order to contribute flexibility to membrane. MSC were seeded on sterilized membranes as described hereinabove.

EC Membranes:

MSC cells showed little adherence to all formulations of EC membranes and cell aggregation was slight. The various plasticizers had no influence on either cell adhesion or cell shape. As control, poly-1-lysine coated membranes were used. Poly-1-lysine, a highly positively charged amino acid chain, is commonly used as a coating agent to promote cell adhesion in culture. Cells adhered in monolayer spindle shape to EC membranes coated with poly-1-lysine, hence it was concluded that EC does not support cell adhesion, as such. However EC was found to be non toxic in the presence of poly-1-lysin.

AMCA Membranes:

Cell adhesion test was performed with Ammonio Methacrylate Copolymer type A (AMCA, EUDRAGIT® RL, Degussa, Germany) [85%], mixed with various plasticizers disclosed herein above [15%].

MSC adhered well to AMCA membranes prepared with the various plasticizers (FIG. 1D-F) in spindle monolayer shape. Cell spreading on the AMCA membranes was similar to spreading on the polystyrene dishes which were used as a positive control for cell adhesion (FIG. 1A-C). The mode of spreading is indicative of the cells' well being.

Cell adhesion was further analyzed using SEM. As shown in FIG. 2 cells on the AMCA membrane, were flat and monolayer spindle shaped. Furthermore, at higher magnification, cell-membrane interaction was seen, with a cellular podia attached to the membrane, (FIG. 2, D-F). Moreover, the release of numerous vacuoles from the cell surface was observed, demonstrating cell functionality. Similar results were obtained using both human as well as rabbit MSC.

Example 2—Cell Proliferation Using a Membrane of the Invention

Proliferative capacity of MSC was tested using the fluorescent marker of cell division, CFSE and flow cytometric analysis. This method is based on the fluorescein related dye CFSE, which is partitioned with remarkable fidelity between daughter cells allowing eight to 10 discrete generations to be identified both in vitro and in vivo. The technique allows complex information on proliferation kinetics and differentiation to be collected According to this technology; individual cells are tagged with the fluorescent CFSE dye that binds irreversibly to cell cytoplasm. As cells divide, their fluorescence halves sequentially with each generation, allowing the proliferative history of any single cell present to be monitored over time (see Lyons AB. Et al [18]).

MSC proliferated on AMCA and PEG 400 membrane (FIG. 3B) (but no proliferation was detected with other plasticizers; data not shown) although at somewhat reduced rates as compared to their proliferative capacity on tissue culture dishes used as control (FIG. 3A).

Figure 4:
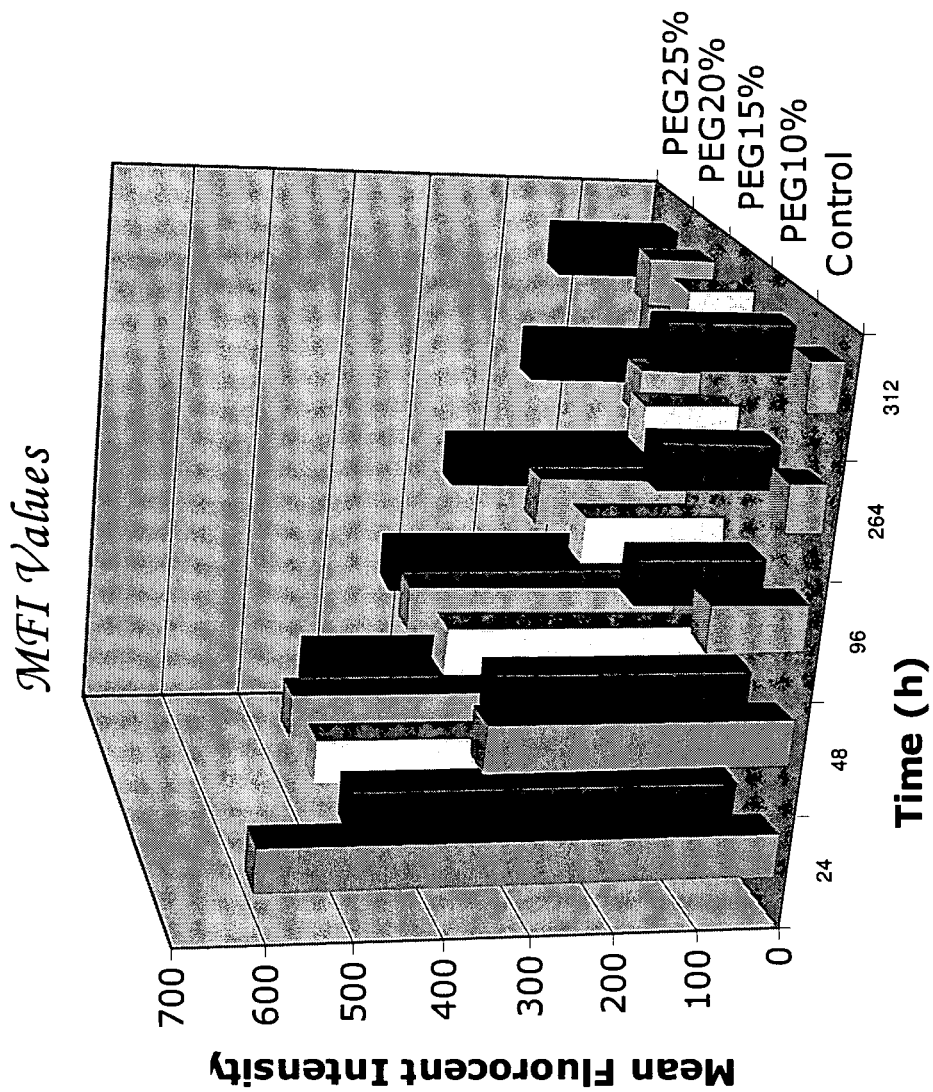
FIG. 4 is a graph showing hMSC proliferation on AMCA membranes prepared with various PEG 400 concentrations. CFSE-loaded hMSC were cultured and analyzed as in FIG. 3. Data are presented as Mean Fluorescent Intensity (MFI) of CFSE over time for AMCA membranes containing different concentrations of PEG 400 vs polystyrene tissue culture dish (control). Decrease in MFI represent rate of MSC proliferation over time.

Subsequently, MSC proliferation rate was tested over time on membranes containing different concentrations of PEG 400 (10%, 15%, 20% and 25% w/w). The rate of MSC proliferation inversely correlated to the mean fluorescent intensity value (MFI) (FIG. 4). This analysis revealed that, membranes containing 15% PEG 400 and 20% PEG 400 were fairly close to the polystyrene control, while other concentrations of PEG resulted in either higher or lower proliferation rates.

In addition, AMCA membrane with 15% and with 5% PEG 400 was characterized using scanning electron microscopy (SEM). Membranes were observed before and after immersion in PBS (FIG. 5). It is noted that membranes were immersed in PBS for 24 hours before each MSC seeding, in order to wash out residual ethanol. Since PEG 400 is soluble in water and thus porogenic, only after immersion in PBS, pores were observed on the membrane surface (FIG. 5B-C). In both concentrations of PEG 400, SEM pictures demonstrated a porous surface, with average pore size of 0.18 µm. Pore distribution correlated directly to different PEG 400 concentrations.

Example 3—Cell Differentiation Using a Membrane of the Invention

Figure 6A:
FIGS. 6A-6B shows hMSC differentiation on AMCA membranes. $1 \times 10^5$ hMSC were cultured on either membrane or polystyrene tissue culture dish. After 3 days when cells reached confluency differentiation medium containing culture medium with ascorbic acid (50 μg/ml), dexamethasone ($10^{-8}$ M) and β-glycerophosphate (10 mM) was added and the cells were fed with fresh differentiation medium twice a week. On the 17th day of culture cells were fixed with 70% ethanol and alizarin red staining was performed.
Figure 6B:
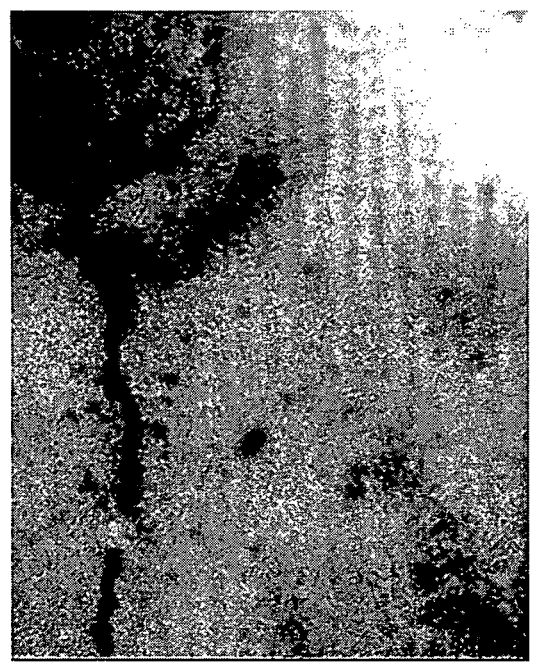

Differentiation medium was added as described hereinabove. Membranes and dishes were then dyed with Alizarin Red. (FIGS. 6A and 6B). Alizarin red binds irreversibly to bivalent positive ions and has especially high affinity towards calcium. Calcium is secreted from osteoblasts and deposits on the membrane as part of the creation of an extracellular matrix. Therefore presence of calcium marks the differentiation from MSC that do not secrete calcium into osteoblast. FIG. 6 demonstrates that MSC cultured on both AMCA membrane and polystyrene controls have differentiated to osteoblast and produced extracellular matrix. This finding confirms that AMCA membrane with 15% PEG 400 supports MSC differentiation and that MSC after adhesion to membrane maintain their stem cells traits.

Example 4—In Vivo Bone Regeneration Study Using a Membrane of the Invention

Study Group:

Five male New Zealand rabbits weighing 3.8-4.4 kg underwent bilateral midshaft resection of radial bone segment (1 cm in length) in forelimbs. Tubular AMCA membranes were implanted in the left forelimb (treated osteotomy) and the right limb served as a control (untreated osteotomy).

Evaluation of Healing Process:

radiographic evaluation—lateral radiographs of forelimbs were obtained 2, 4, 6 and 8 weeks postoperatively. To obtain standardized measurements of the bone defects during the regenerative healing process, true lateral radiographs of both forelimbs were performed in standard conditions (42 kV, 2 mas). Radiographs were examined using OsiriX medical imaging software to evaluate the area and density of the new bone.

Measured Parameters:

Total area of regenerated bone tissue (appearing around and within the bone gap defect). To eliminate possible bias by variability of bone dimensions, data calibration was made using the diameter of olecranon process at its narrowest zone as a standard reference. This diameter was defined as 10 mm in each specimen.

Relative density of the newly regenerated bone in the gap defect. The segmented area was outlined, and the density was measured. The bone density in the center of the olecranon process was measured in each forelimb for a calibration, as a reference value. The density of olecranon process was defined as a 100% for each specimen (see Mosheiff R. et al. [10]).

Figure 7:
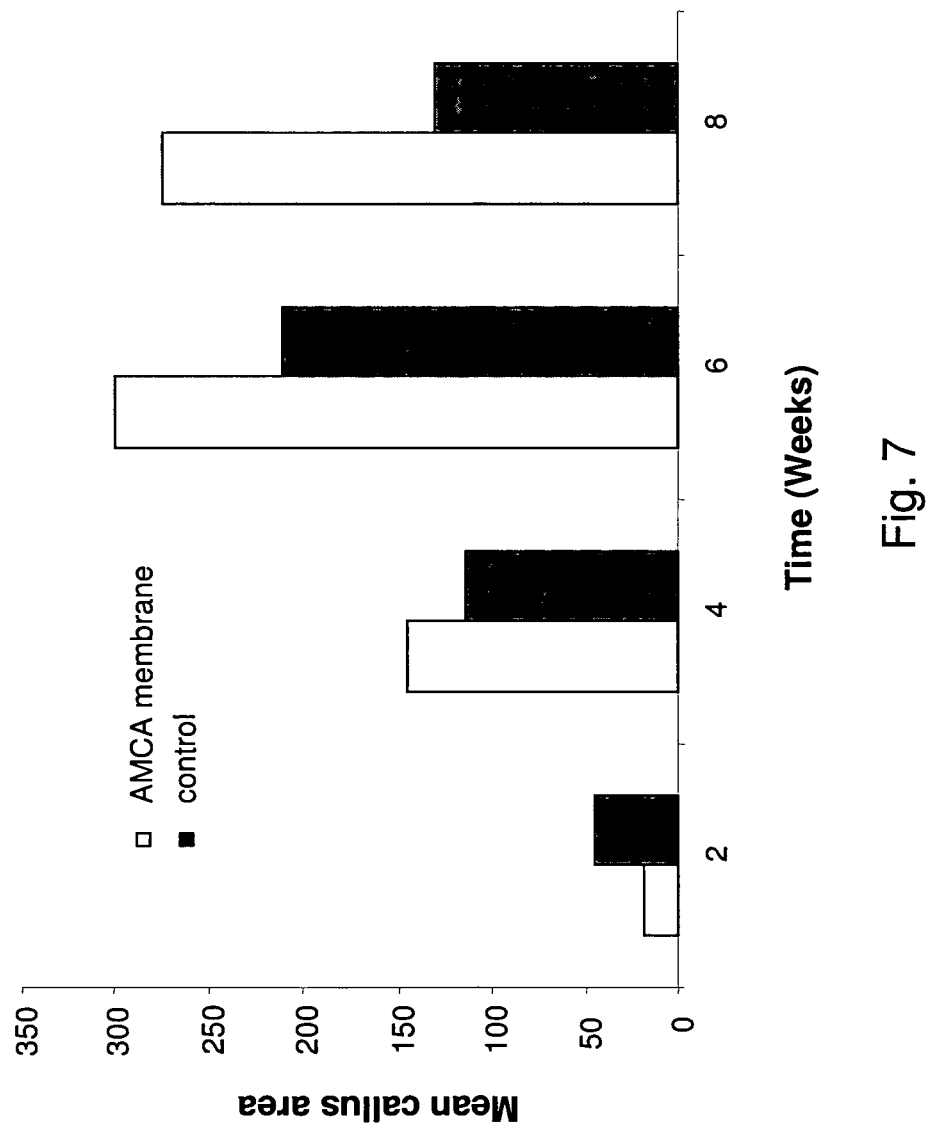
FIG. 7 is a graph showing bone regeneration by mean callus area. An increased mean callus area was measured in bones implanted with AMCA membranes as compared to untreated controls.

Results:

FIG. 7 shows bone regeneration expressed by mean callus area (mm$^2$) throughout the study (weeks 2 to 8). At week 2 of the study the mean callus area produced in control arm was larger then that of arm treated with AMCA membrane, possibly due to formation of hematome or blood clot at the surgery site. When the site was surrounded by membrane it isolated the area and thus slowed the degradation of the hematome. However from week four of the study, mean area of callus generated in the limb treated with AMCA membrane was slightly bigger than that of the control (144.8 mm$^2$ vs. 114.5 mm$^2$). This trend continued at weeks 6 and 8, hand in hand with widening the difference between mean callus areas of AMCA membrane treated limb and control limb. At week 8, the difference between mean callus areas produced in two limbs (treated with AMCA membrane and control) reached its peak and was 143.91 mm$^2$ (see Table 1 below). However, this difference is not statistically significant, due to small sample size (n=5) of this preliminary study and high variability of results, as it often happens in in vivo studies.

TABLE 1

Radiographic parameters of the study at week 8 (end point)

| Measured parameter | sig (2-tailed) | mean Difference (mm$^2$) | std | control mean (mm$^2$) | std | AMCA membrane mean (mm$^2$) |
|---|---|---|---|---|---|---|
| surface area of callus | 0.08 | 143.91 | 85.633 | 129.74 | 277.203 | 273.65 |
| relative density of callus | 0.68 | 20.54 | 39.8 | 123.33 | 101.95 | 143.87 |
| relative density of prox quad | 0.89 | 31.96 | 38.35 | 126.12 | 107.43 | 158.08 |
| relative density of prox med quad | 0.68 | 55.84 | 51.93 | 96.44 | 126.81 | 152.28 |
| relative density of distal med quad | 0.34 | 57.89 | 37.7 | 106.28 | 114.28 | 164.17 |
| relative density of distal quad | 0.5 | 40.41 | 41.99 | 110.07 | 88.78 | 150.48 |

Figure 8A:
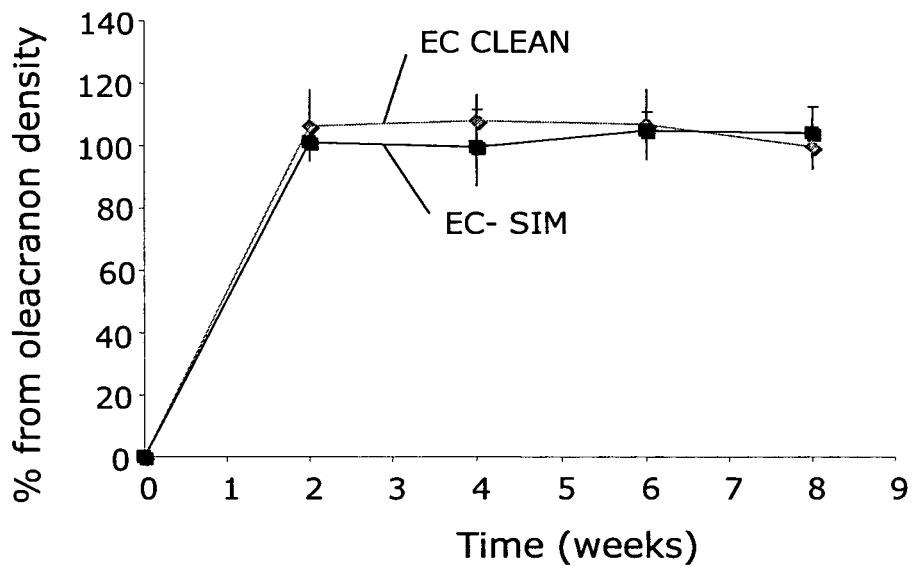
FIGS. 8A-8B is a graph showing quantitative analysis of relative callus density changes over time (FIG. 8A) and callus area changes over time (FIG. 8B) observed for ethyl cellulose membrane and ethyl cellulose membrane controllably releasing simvastatine in 6 male New Zealand rabbits for which critical size defect (10 mm) was created in both forelimbs. Forelimb was inserted with Ethyl Cellulose (EC)
Figure 8B:
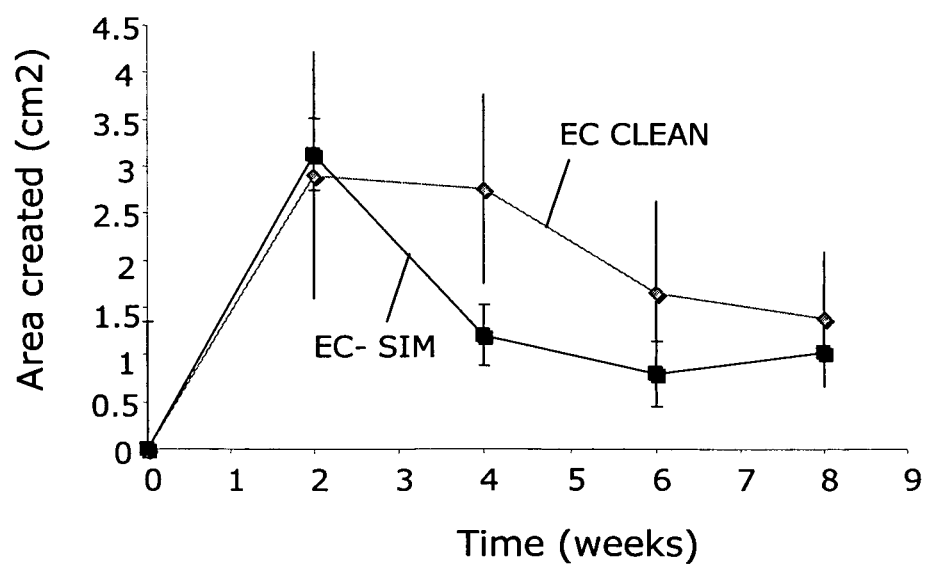

Example 5—In Vivo Bone Regeneration Study Using an EC Membrane of the Invention Further Comprising Simvastatin In 6 male New Zealand rabbits critical size defect (10 mm) was created in both forelimbs. In one forelimb EC membrane which contained simvastatin was inserted, in the contralateral limb EC membrane with no active agent was inserted. Callus density and Callus area were measured and calibrated using Osirix software. FIGS. 8A and 8B show the quantitative analysis of the radiographs.

FIG. 9 shows the microCT of bone regeneration with EC membrane. In this experiment bone defect was left untreated. The bone defect is in non union state. Arrows mark the bone defect area.

FIG. 10 shows microCT of bone regeneration with EC membrane containing simvastatin. Arrows mark the bone defect area.

In this experiment bone defect was treated and successful bridging of the defect is evident.

Example 6—In Vivo Bone Regeneration Study Using an AMCA Membrane of the Invention Further Comprising Simvastatin Rabbit Model:

critical size bone defect of 1 cm in radius bone were created. 5 rabbits were treated with simvastatin controlled release AMCA membrane and 5 others with AMCA membrane without any active ingredient.

Membranes:

AMCA membrane comprising simvastatine:
Simvastatin 20% w/w—0.36 g
AMCA (EUDRAGIT® RL) 70% w/w—1.26 g PEG 400 10% w/w—0.18 g
Membrane width was 180 micrometer.
Control AMCA membrane:
AMCA (EUDRAGCIT® RL) 90% w/w—1.26 g
PEG 400 10% w/w—0.18 g
Membrane width was 180 micrometer.

FIG. 11 shows significantly larger callus area formed at the defect site treated with simvastatin controlled release AMCA membrane (Wilcoxon summed ranks test), as well as increase in callus growth rate at 2 first post operation weeks—may be important from clinical point of view.

Figure 12A:
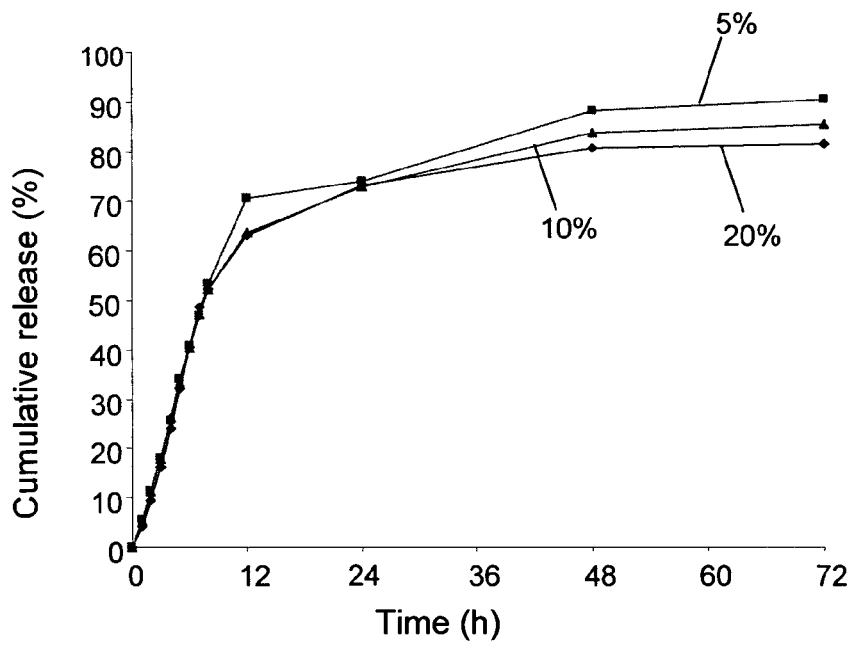

Example 7—In Vitro Release Rate of Simvastatin from Different Membranes of the Invention The effects of various parameters on simvastatine release from membranes of the invention were measured in vitro as follows:

The effect of simvastatin concentration on simvastatin release rate is shown in FIG. 12A; the composition of the tested membranes was as follows:

| Membrane components | Membrane 1 | Membrane 2 | Membrane 3 |
|---|---|---|---|
| Simvastatin | 20% | 5% | 10% |
| PEG 400 | 10% | 10% | 10% |
| EUDRAGIT® RL | 70% | 85% | 80% |
| width (micron) | 90 | 75 | 87 |

Figure 12B:
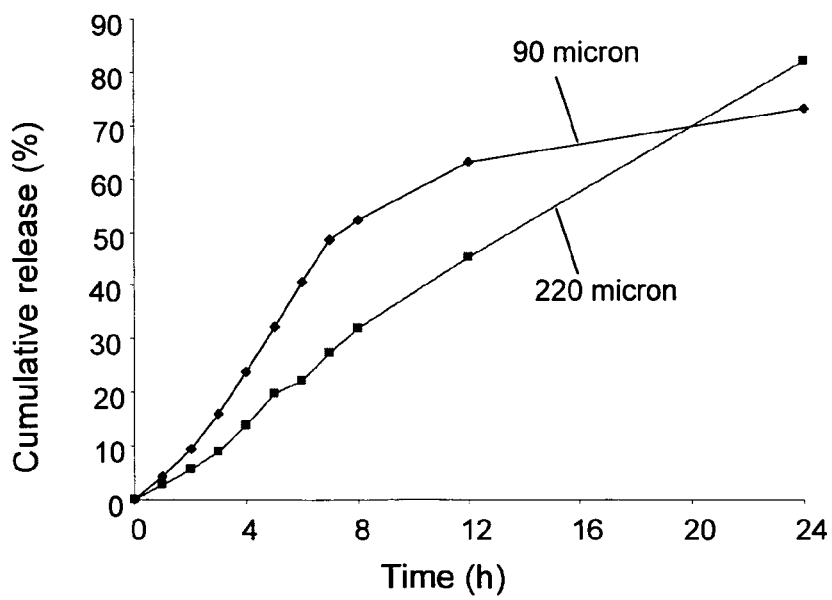

The effect of membrane width on simvastatin release rate is shown in FIG. 12B; the composition of the tested membranes was as follows:

| Membrane components | Membrane 4 | Membrane 5 |
|---|---|---|
| Simvastatin | 20% | 20% |
| PEG 400 | 10% | 10% |
| EUDRAGIT® RL | 70% | 70% |
| width (micron) | 90 | 220 |

Figure 12C:
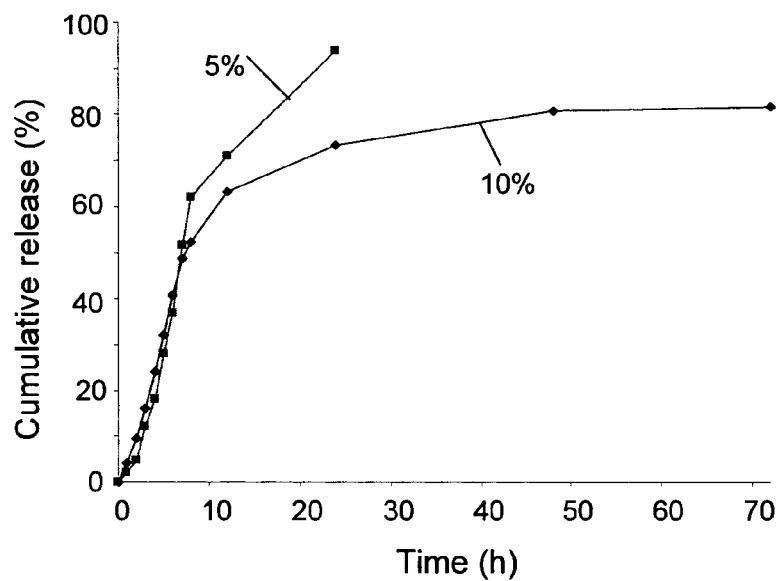
Figure 12D:
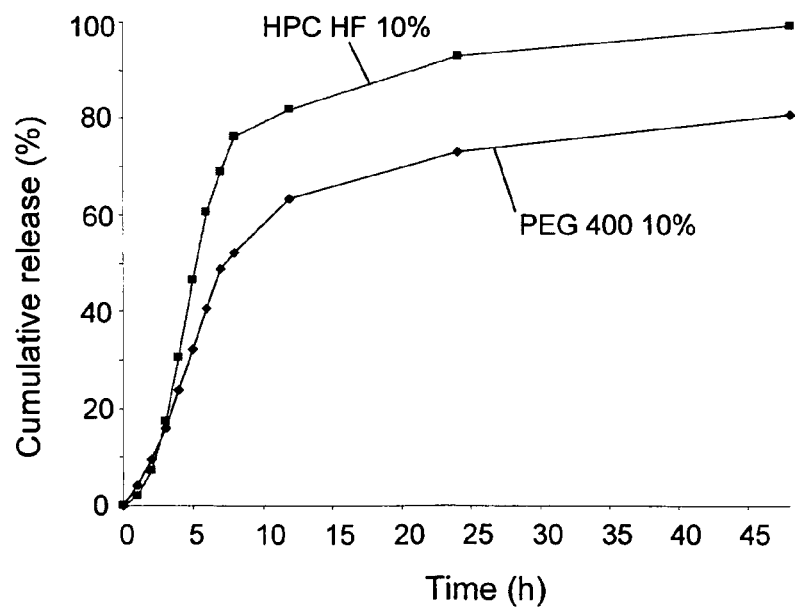

The effect of plasticizer on simvastatin release rate is shown in FIG. 12C; the composition of the tested membranes was as follows:

| Membrane components | Membrane 6 | Membrane 7 | Membrane 8 |
|---|---|---|---|
| Simvastatin | 20% | 20% | 20% |
| PEG 400 | 10% | 5% | 10% - Klucel HF |
| EUDRAGIT® RL | 70% | 75% | 70% |
| width (micron) | 90 | 104 | 87 |

The effect of plasticizer type on simvastatin release rate is shown in FIG. 12D.

Example 8—Bone Regeneration with AMCA Membrane Comprising HMSC

Rabbit Model:
critical size bone defect of 1 cm in radius bone was created. Two rabbits were treated with AMCA membrane carrying hMSC in one forearm and on another forearm AMCA membrane without hMSC.
Properties of the Membrane:
AMCA (EUDRAIGIT® RL) 85% w/w—1.512 g
PEG 400 15% w/w—0.266 g
Membrane width was of 180 micrometer.

FIG. 13A demonstrates the development of the callus area in the effected bone. As shown in FIG. 13B the histological score of various parts of the defected bone area at 8 weeks post operation is higher in bones implanted with an AMCA membrane carrying hMSC.

REFERENCES

1. Gerstenfeld L C, Cullinane D M, Barnes G L, Graves D T, Einhorn T A. Fracture healing as a post-natal developmental process: molecular, spatial, and temporal aspects of its regulation. J Cell Biochem 2003; 88(5):873-84.
2. Megas P. Classification of non-union. Injury 2005; 36 Suppl 4:S30-7.
3. Crenshaw H. Delayed union and non-union of fractures. St. Louis: C V Mosby; 1987. 2053-118 p.
4. Hernigou P, Poignard A, Beaujean F, Rouard H. Percutaneous autologous bone-marrow grafting for nonunions. Influence of the number and concentration of progenitor cells. J Bone Joint Surg Am 2005; 87(7):1430-7.
5. Kraus K H, Kirker-Head C. Mesenchymal stem cells and bone regeneration. Vet Surg 2006; 35(3):232-42.
6. Cancedda R, Mastrogiacomo M, Bianchi G, Derubeis A, Muraglia A, Quarto R. Bone marrow stromal cells and their use in regenerating bone. Novartis Found Symp 2003; 249:133-43; discussion 143-7, 170-4, 239-41.
7. Cancedda R, Dozin B, Giannoni P, Quarto R. Tissue engineering and cell therapy of cartilage and bone. Matrix Biol 2003; 22(1):81-91.
8. Tsuchiya K, Mori T, Chen G, Ushida T, Tateishi T, Matsuno T, Sakamoto M, Umezawa A. Custom-shaping system for bone regeneration by seeding marrow stromal cells onto a web-like biodegradable hybrid sheet. Cell Tissue Res 2004; 316(2):141-53.
9. Meinig R P, Rahn B, Perren S M, Gogolewski S. Bone regeneration with resorbable polymeric membranes: treatment of diaphyseal bone defects in the rabbit radius with poly(L-lactide) membrane. A pilot study. J Orthop Trauma 1996; 10(3):178-90.
10. Mosheiff R, Friedman A, Friedman M, Liebergall M. Quantification of guided regeneration of weight-bearing bones. Orthopedics 2003; 26(8):789-94.
11. Ito K, Nanba K, Murai S. Effects of bioabsorbable and non-resorbable barrier membranes on bone augmentation in rabbit calvaria. J Periodontol 1998; 69(11):1229-37.
12. Nasser N J, Friedman A, Friedman M, Moor E, Mosheiff R. Guided bone regeneration in the treatment of segmental diaphyseal defects: a comparison between resorbable and non-resorbable membranes. Injury 2005; 36(12): 1460-6.
13. Friedman M, Golomb G. New sustained release dosage form of chlorhexidine for dental use. I. Development and kinetics of release. J Periodontal Res 1982; 17(3):323-8.
14. Krampera M, Glennie S, Dyson J, Scott D, Laylor R, Simpson E, Dazzi F. Bone marrow mesenchymal stem cells inhibit the response of naive and memory antigen-specific T cells to their cognate peptide. Blood 2003; 101(9):3722-9.
15. Djouad F, Plence P, Bony C, Tropel P, Apparailly F, Sany J, Noel D, Jorgensen C. Immunosuppressive effect of mesenchymal stem cells favors tumor growth in allogeneic animals. Blood 2003; 102(10):3837-44.
16. Barry F P, Murphy J M. Mesenchymal stem cells: clinical applications and biological characterization. Int J Biochem Cell Biol 2004; 36(4):568-84.

17. Halvorsen Y D, Franklin D, Bond A L, Hitt D C, Auchter C, Boskey A L, Paschalis E P, Wilkison W O, Gimble J M. Extracellular matrix mineralization and osteoblast gene expression by human adipose tissue-derived stromal cells. Tissue Eng 2001; 7(6):729-41.
18. Lyons A B. Analysing cell division in vivo and in vitro using flow cytometric measurement of CFSE dye dilution. J Immunol Methods 2000; 243(1-2):147-54.
19. Gugala Z, Gogolewski S. Differentiation, growth and activity of rat bone marrow stromal cells on resorbable poly(L/DL-lactide) membranes. Biomaterials 2004; 25(12):2299-307.
20. Aggeliki I. et al Macromolecules, 35 (7), 2506-2513, 2002.

The invention claimed is:

1. A sterile surgical implant for implantation within a subject, consisting of a homogenous membrane and, optionally, at least one type of cell, wherein said homogenous membrane comprises:
    at least one positively charged synthetic, hydrophobic polymer;
    at least one hydrophilic polymer, and
    at least one plasticizer, wherein said plasticizer is polyethylene glycol ranging from 300-20,000,
    and, optionally, at least one active agent.

2. A sterile surgical implant according to claim 1, wherein both said hydrophilic polymer and said plasticizer are polyethylene glycol ranging from 300-20,000.

3. A sterile surgical implant according to claim 2, wherein said at least one hydrophilic polymer is present in a concentration of between about 1% (w/w) to 30% (w/w) of the membrane.

4. A sterile surgical implant according to claim 1, wherein both said hydrophilic polymer and said plasticizer are polyethylene glycol 400.

5. A sterile surgical implant according to claim 4, wherein said polyethylene glycol 400 is present at a concentration of 5%, 10%, 15%, 20% or 25% w/w.

6. A sterile surgical implant according to claim 4, wherein said at least one hydrophilic polymer is present in a concentration of between about 1% (w/w) to 30% (w/w) of the membrane.

7. A sterile surgical implant according to claim 1, wherein said at least one hydrophilic polymer is present in a concentration of between about 1% (w/w) to 30% (w/w) of the membrane.

8. A sterile surgical implant according to claim 1, further consisting of at least one type of cell.

9. A sterile surgical membrane according to claim 8, wherein said cells are selected from the group consisting of adult stem cells, embryonic stem cells, pluripotent stem cells, mesenchymal stem cells, umbilical cord blood cells, osteoblasts, chondroblasts and CD105+ cells.

10. A sterile surgical implant according to claim 9, wherein said cells are autologous adult stem cells.

11. A sterile surgical implant according to claim 1, further consisting of at least one active agent, wherein said at least one active agent is selected from the group consisting of cytokine, hormone, bisphosphonate, cannabinoid, beta blocker, bone inducing agent, growth factor, HMG-CoA reductase inhibitor, drug and antibiotic.

12. A sterile surgical implant according to claim 11, wherein said active agent is selected from the group consisting of statin, estrogen, androgen, propranolol, transforming growth factor (TGF), bone morphogenetic protein (BMP), insulin like growth hormone, fibroblast growth factor (FGF), alendronate, risedronate and parathyroid hormone.

13. A sterile surgical implant according to claim 12, wherein said active agent is simvastatin or lovastatin.

14. A sterile surgical implant according to claim 1, wherein said membrane becomes porous upon hydration, and wherein the pore size is between about 0.1 to about 5 microns.

15. A sterile surgical implant according to claim 1, wherein said hydrophobic polymer is a methacrylate copolymer substituted by at least one amine group.

16. A sterile surgical implant according to claim 15, wherein said positively charged synthetic, hydrophobic polymer is ammonio methacrylate copolymer type A NF (AMCA).

17. A sterile surgical implant according to claim 1 which has a three dimensional shape formed without pre-casting, re-molding, or exposure to heat.

18. A sterile surgical implant according to claim 1 which has a three dimensional, hollow shape.

19. A sterile surgical implant according to claim 18 which has a three dimensional, hollow tubular shape.

20. A sterile surgical implant according to claim 1, wherein the membrane is hydrated upon implantation.

21. A sterile surgical implant according to claim 1, wherein said membrane has a thickness of between 30 and 200 m.

22. A sterile surgical implant according to claim 1, wherein said membrane has a thickness of 75, 87, 90, 104, 180 or 220 m.

23. A sterile surgical implant for implantation within a subject, consisting of a membrane and, optionally, at least one type of cell, wherein said membrane consists of:
    at least one positively charged synthetic, hydrophobic polymer;
    at least one hydrophilic polymer, and
    at least one plasticizer, wherein said plasticizer is polyethylene glycol ranging from 300-20,000.

24. A sterile surgical implant for implantation within a subject, consisting of a membrane and, optionally, at least one type of cell, wherein said membrane consists of:
    at least one positively charged synthetic, hydrophobic polymer;
    at least one hydrophilic polymer,
    at least one plasticizer, wherein said plasticizer is polyethylene glycol ranging from 300-20,000; and
    at least one active agent selected from the group consisting of cytokine, hormone, bisphosphonate, cannabinoid, beta blocker, bone morphogenetic protein (BMP), growth factor, HMG-CoA reductase inhibitor, antibiotic, statin estrogen, androgen, propranolol, transforming growth factor (TGF), insulin like growth hormone, fibroblast growth factor (FGF), alendronate, risedronate, parathvroid hormone, simvastatin, lovastatin, and combinations thereof.

25. A sterile surgical implant according to claim 24, wherein said active agent is selected from the group consisting of statin, estrogen, androgen, propranolol, transforming growth factor (TGF), bone morphogenetic protein (BMP), insulin like growth hormone, fibroblast growth factor (FGF), alendronate, risedronate, parathyroid hormone, and combinations thereof.

26. A sterile surgical implant according to claim 25, wherein said active agent is simvastatin or lovastatin.

* * * * *